(12) United States Patent
Mielcarek et al.

(10) Patent No.: US 6,660,261 B1
(45) Date of Patent: Dec. 9, 2003

(54) BORDETELLA STRAIN EXPRESSING THE FHA HYBRID, LIPOSOMES AND VACCINES

(75) Inventors: Nathalie Mielcarek, Lille (FR); Camille Locht, Wannehain (FR); Gilles Riveau, Lille (FR); Odile Poulain-Godefroy, Lambersart (FR); André Capron, Phalempin (FR)

(73) Assignee: Institut Pasteur de Lille, Lille (FR)

( * ) Notice: Subject to any disclaimer, the term of this patent is extended or adjusted under 35 U.S.C. 154(b) by 0 days.

(21) Appl. No.: 09/284,252

(22) PCT Filed: Oct. 9, 1997

(86) PCT No.: PCT/FR97/01802
§ 371 (c)(1),
(2), (4) Date: Sep. 16, 1999

(87) PCT Pub. No.: WO98/16553
PCT Pub. Date: Apr. 23, 1998

(30) Foreign Application Priority Data

Oct. 11, 1996 (FR) .............................................. 96 12461

(51) Int. Cl.$^7$ ........................ A01N 63/00; A61K 39/02; A61K 39/10; A61K 39/00
(52) U.S. Cl. .................. 424/93.4; 424/93.2; 424/200.1; 424/203.1; 424/184.1; 424/254.1; 424/234.1; 424/242.1
(58) Field of Search ........................... 424/200.1, 203.1, 424/242.1, 254.1, 253.1, 282.1, 450, 234.1, 184.1, 269.1, 278.1, 93.1, 93.2, 93.4; 435/69.7, 69.1, 69.3

(56) References Cited

U.S. PATENT DOCUMENTS 6,036,960 A * 3/2000 Relman et al. ........... 424/253.1
6,040,427 A * 3/2000 Locht et al. ................. 530/350

FOREIGN PATENT DOCUMENTS

| EP | 0 159 003 | 10/1985 |
| EP | 0 322 115 | 6/1989 |
| EP | 0 396 964 | 11/1990 |
| EP | 0471954 | * 2/1992 |
| EP | 0 629 696 | 12/1994 |
| EP | 0 688 868 | * 12/1995 |
| WO | WO 87/03301 | 6/1987 |
| WO | WO 90/13313 | * 11/1990 |
| WO | WO 92/05194 | * 4/1992 |
| WO | WO 95/28486 | 10/1995 |

OTHER PUBLICATIONS

Reiser et al. Dev. Biol. Stand. 61: 265–271, 1985 (abstract).*
Domenighini et al. Mol. Microbiol. 4: 787–800, 1990 (abstract).*
Lee et al. Infect. Immun. 57: 1413–1418, 1989 (abstract).*
Shahin et al. Infect. Immun. 60: 1482–1488, 1992 (abstract).*
Novotny et al. J. Infect. Dis. 164: 114–122, 1991.
Cockle et al. In: Immunobiology of Proteins and Peptides VI,. (Ed) Atassi MZ. Plenum Press, New York, 221–225, 1991.
Mooi FR. Antonie van Leeuwenhoek 54: 465–474, 1988.
Weiss et al. Infect. Immun. 42: 33–41, 1983.
Carbonetti et al. J. Bacteriol. 175: 6679–6688, 1993.*
Novotny et al. In: Abstracts of the International Workshop on *Bordetella pertussis*. Rocky Mountain Laboratories, Hamilton, Montana, Aug. 18–20, 1988.*
Olander et al. Microbial Pathogenesis 8: 37–45, 1990.*
Poolman et al. In: Proceedings of the Sixth International Symposium on Pertussis. National Institutes of Health, Bethesda, MS Sep. 26–28, 1990, pp. 148–156.*
W.J. Black et al., "Construction and Characterization of *Bordetella pertussis* Toxin Mutants", XP 002035137, Infection and Immunity, vol. 55, No. 10, pp. 2465–2470, (1987).
N. Mielcarek et al., "Intranasal Priming with Recombinat *Bordetella pertussis* for the Induction of a Systemic Immune Response against a Heterologous Antigen", XP 002035138, Infection and Immunity, vol. 65, No. 2, pp. 544–550, (1997).
M. Drescher et al., "Recovering protective antigens from crude Bordetella extracts—by affinity chromatography on lectin contg. carrier, useful as vaccines and diagnostic reagents", XP 002035139, Derwent Publications, Ltd., London, GB, (1989). DD 268161 A.
C.R. Manclark et al., "Protecting against *bordetella pertussis* or bronchiseptica—by mucosal administration of vaccine contg. outer membrane or filamentous haemagglutinin protein", XP 002035140, Derwent Publications, Ltd., London, GB, (1991). VS 7532327 A.
G. Renauld–Mongénie et al., Induction of mucosal immune responses against a heterologous antigen fused to filamentous hemagglutinin after intranasal immunization with recombinant *Bordetella pertussis*, XP 002035136, Proc. Natl. Acad. Sci. USA, vol. 93, pp. 7944–7949, (1996).

* cited by examiner

*Primary Examiner*—S. Devi
(74) *Attorney, Agent, or Firm*—Finnegan, Henderson, Farabow, Garrett & Dunner, L.L.P.

(57) ABSTRACT

The invention concerns a Bordetella strain deficient in the production of toxin and expressing a hybrid protein comprising at least part of the filamentous hemagglutin (FHA) and at least part of a protein heterologous to FHA. The gene coding for the toxin has been eliminated, or at least partially deleted or mutated so as to produce an inactive toxin. This strain can be used as vaccine. The invention also concerns liposomes containing at least part of the FHA protein and at least one protein heterologous to the FHA protein, and the use of FHA for the stimulation of immune responses.

8 Claims, 13 Drawing Sheets

BORDETELLA STRAIN EXPRESSING THE FHA HYBRID, LIPOSOMES AND VACCINES

This application is a U.S. national stage application of PCT/FR97/01802, filed Oct. 9, 1997, which claims priority to French Application number 96/12461, filed Oct. 11, 1996.

BACKGROUND OF THE INVENTION

Pertussis, the most responsible agent of which is the gram-negative bacterium Bordetella pertussis, remains a current infectious disease throughout the world. More than 50 millions cases are declared each year and a mortality estimation is 500 000 deaths per year, mainly infants. Mortality is for example high in the developing countries where vaccination is not sufficient and pertussis represents one of the major causes of infantile mortality. The advent of cellular vaccines consisting in chemically or thermally inactivated B. pertussis has led to a spectacular reduction of pertussis occurrence. However, limitations related to their use have appeared during these last two decades. Various reports have thus put forward the hypothesis of a relationship between the administration of the cellular vaccine against pertussis and some serious side-effects.

Moreover, the need to administrate various vaccinal doses to obtain a maximum protection, the variability of efficiency of the different batches of vaccines and the resurgence of the disease in adults due to a weakening of post-vaccinal immunity during the period of the post-vaccinal immunity in the absence of late re-vaccinations are as many inconveniences that have led to the development of cellular vaccines. However, the protective antigens comprising those new generation vaccines, generally defined as more efficient, more secure and more immunogenic than cellular vaccines, have not been clearly defined yet and multiple injections are still necessary. Moreover, serological correlations with the protection of children have not still been determined. Finally, the production cost of these vaccines has been found higher than this of the prior ones, which represents an important problem for developing countries that are most demanding.

On the other hand, it has been shown that the natural infection with B. pertusiss leads to a long-term protection, whereas the one induced by vaccination had a limited time (Bass, J. W. et al. 1987 Pediatr. Infect. Dis. J. 6:141–144, Jenkinson, D. 1988, Br. Med. J. 296:612–614). The reasons for this difference are not clear, showing the lack of knowledge relating to immunizing mechanisms involved in each case. One of the potential explanations is based upon a better induction of the immunologic memory at the respiratory tract after an infection, compared to the one obtained after a parenteral immunization. Moreover, a Th1-type cellular response T, which could play an important part in the protective immunity, is induced through the natural infection, whereas immunization with the cellular vaccine shows rather a strong response Th2 (Mills, K. H. G. et al. 1983, J. Med. Microbiol. 39:163–164). Finally, the infection stimulates IgA production against B. pertussis antigens in the serum and the secretions, whereas these antibodies are not frequently detected on vaccinated individuals (Shahin, R. et al. 1992, in J. E. Ciardi et al. Eds Genetically Engineered Vaccines, Plenum Press N.Y.).

All those observations led to the belief that a long-term protection against pertussis would be better obtained through a vaccination with attenuated living bacteria administrated at the level of the respiratory mucosas, which are the natural openings during the infection by B. pertussis. Prior work has shown that immunization of mice either with spontaneous attenuated living strains (Vesselinova-Jenkins, C. K., 1985. Dev. Biol. Stand. 61:517–524) or aroA strains (Roberts, F. et al. 1990. Infect. Immun. 58:732–739) of B. pertussis protects against a second infection. However, such strains are inconvenient in that they are badly characterized and hold a certain toxicity, or have lost to a great extent their colonizing capacity, and thus require numerous administrations to induce an efficient protective immunity.

The B. pertussis toxin is an oligomer protein formed with five sub-units so-called S1 to S5. It may be shared into two great domains so-called protomer A (consisting in S1) and oligomer B (consisting in S2 to S5). The oligomer B is responsible for the toxin interaction with its receptors at the surface of the target cells and the protomer A (or S1) is injected into the target cell and expresses therein an ADP-ribosyltransferase enzyme activity (Tamura et al., Biochemistry 21, 5516–5522, 1962). The genes coding for the five sub-units have been cloned and sequenced (Locht and Keith, Science 232, 1258–1264, 1986) and the crystal structure has been established (Stein et al., Structure 2, 45–47, 1994). Various mutations in the toxin gene have been described as being responsible for the genetic inactivation of this molecule. These mutations may be found in S1 gene (review, see Locht and Antoine, Biochimie 77, 333–340, 1995) and/or in the genes coding for the oligomer B (see for example Lobet et al. J. Exp. Med. 177, 79–87, 1993). The toxin may be put in evidence through an immunologic activity with polyclonal or monoclonal antibodies, such as for example the antibody 1B7 mentioned thereafter or through its biological activity, such as the activity on the cells "Chinese Hamster Ovary" as described by Hewlett et al. (Infect. Immun. 40, 1198–1203, 1983).

Filamentous hemagglutinin (FHA) is the major adhesion produced and secreted by B. pertussis (review, see Locht et al. Mol. Microbiol., 9, 653–660, 1993). The structure gene of the FHA, so-called fhaB, has been clond (Brown, D. R. et al. 1987. Infect. Immun. 55:154–161; Relman, D. A. et al. 1989. Proc. Natl. Acad. Sci. USA. 86:2637–2641; Delisse-Gathoye, A.M. et al. 1990. Infect. Immun. 58:2895–2905) and codes for a precursor (FHAB) of about 367 kDa. The mature form (220 kDa) corresponds to the N-terminal two thirds of FHAB and has a structure so-called "hair pin" (Makhov et al., J. Mol. Biol. 241, 110–124, 1994). Although the C-terminal part of FHAB is not present under the mature form, it has interesting characteristics such as various regions known to be rich in proline and an RGD site. Moreover, this C-terminal part of the precursor appears to play an important part in FHA secretion. Downwards the N-terminal region of the FHA two repetitive regions, respectively A and B, are located, followed by a proteolysis-sensitive site and by a RGD sequence. The FHAB maturation site is located at about 1000 amino-acids downwards this RGD sequence. The FHAB N-terminal domain plays an essential part in the secretion of the mature protein since a phase deletion of this region appears to inhibit totally the FHA biogenesis. The FHA secretion depends upon a minor protein so-called-FhaC present at the level of the external membrane of B. pertussis. This protein is coded by the gene FhaC located downwards FhaB and separated from this latter by three other genes, fimB, fimC and fimD, coding for the fimbriae. An FHA secretion mechanism involving cleavage and then modification of the N-terminal part of FHAB, followed by interaction between this region and the minor protein FHAC, have been proposed.

The various FHA binding mechanisms allow the B. pertussis to adhere to numerous types of eukaryote cells.

Although the B. pertussis toxin is involved in the adherence of the bacterium with the epithelial cells of the respiratory tract, the FHA plays a major part in such an interaction. The FHA can interact with glycoconjugates and the carbohydrate recognition domain has been identified in the FHA region limited by the amino-acids 1141 to 1279 which would correspond to the buckle of the "hair-pin" structure which already contains the RGB site in positions 1097–1099. The FHA is also the major adhesin involved in the adherence mechanism of B. pertussis with the unciliated epithelial cells. An activity of binding this molecule to the heparin sulphated glycosaminoglycan, present in non negligible amount in the bronchial mucus as well as in the extracellular matrix and at the surface of numerous epithelial cells is responsible for the bacterium adherence with these cells. Recent studies make obvious a specific heparin binding site located in the N-terminal region of the FHA, probably in the region comprised between the amino-acids 442 and 863 (Hannah et al. Infect. Immun., 62, 5010–5019, 1994).

Besides this adherence activity on the ciliated and unciliated epithelial cells, FHA is able to bind specifically with the CR3 (CD11b/CD18, aMb2) present on the macrophages and monocytes (Relman et al. Cell, 61, 1375–1382, 1990). This binding of B. pertussis, via the FHA, with the CR3 allows for the internalization of these bacteria in the macrophages through a means generating no oxidative catabolism.

Due to its interest in the adherence of B. pertussis with various cell types, the FHA has been considered as a major antigen for vaccination against pertussis. Administrating a cellular vaccine to mice or children leads to the production of anti-FHA antibodies in their serum. Moreover, vaccinating 18 month old children with a cellular vaccine induces high rates of anti-FHA antibodies as well as specific cellular response T. These immune characteristics are found in convalescent people after a pertussis.

However, the isotopic profile of the anti-FHA response in children having received the cellular vaccine differs from the one of individuals attacked by pertussis. Whereas the specific serous immunoglobulin G rate (IgG) is similar, the anti-FHA IgA2 response is more important in sick people than in vaccinated people. This difference is still more marked at the level of nasopharyngeal secretions and saliva, where an increase of the anti-FHA IgA rate is observed in most of the patients various weeks after the beginning of the symptoms. Similarly, high anti-FHA IgA rates are found in the nasal secretions of mice infected with the B. pertussis virulent strain in a period up to 26 weeks after the infection. An immune response both IgAs and IgG against the FHA may also be obtained in the respiratory tract of mice after an intranasal vaccination with purified FHA.

Potentially protective epitopes of cells B and T have been localized on the FHA. An immunodominant region has been thus determined in the C-terminal region of the mature FHA. It is recognized by the murine cells B and by the human lymphocytes T CD4+ which also recognize the N-terminal part of the FHA.

Recombinant fusion proteins comprising one part of the FHA and heterologous peptides have been described in the French application FR 94 04661 (published under the No. 2 718 750) (INSTITUT PASTEUR, INSTITUT PASTEUR DE LILLE, INSERM). In this application, recombinant DNAs comprising a sequence coding for a heterologous polypeptide, fused in the same reading frame with a sequence coding for at least a part of the FHA precursor, are prepared and expressed in cell cultures, particularly Bordetella detoxified or attenuated cultures.

SUMMARY OF THE INVENTION

This invention relates to a Bordetella strain deficient in the production of toxins and expressing a hybrid protein.

It also relates to liposomes comprising at least a heterologous protein and at least one part of the FHA (filamentous hemagglutinin) protein.

It also relates to the immunoprophylactic and/or therapeutic uses thereof, particularly as vaccines.

In addition, the invention relates to the use of FHA for stimulating an immune response.

One of the objects of this invention is to expose the recombinant peptide at the surface of prokaryote cells, particularly for vaccination purposes. It should be noted that detoxification or attenuation of recombinant cells is only mentioned accessorily and that further neither an example nor a particular procedure illustrates this possibility. In particular, this invention does not mention accurately how the cells are detoxified or attenuated.

Thus, it results from the analysis of the prior art that vaccination means against pertussis have been known before, but that they induced side-effects.

The applicant had thus made efforts to find vaccination means against pertussis, but also against other pathogens, deprived of side-effects, easy to implement and able to be produced at low cost.

We have first found surprisingly that an intranasal administration of a strain deprived of B. pertussis toxin gene induced a high production of antibodies directed against the filamentous hemagglutinin (FHA) and that it was consequently possible to stimulate the immune response against a heterologous antigen fused with the FHA.

We have found on the other hand that the FHA integrated into liposomes containing other peptides having epitopes, improved the binding of these liposomes with the mucosas of the respiratory tract.

We have finally found that the FHA had generally immunostimulating properties.

DETAILED DESCRIPTION OF THE INVENTION

The present invention relates thus first to a Bordetella strain deficient in the production of toxins and expressing a hybrid protein comprising at least one part of the filamentous hemagglutinin (FHA) and at least one part of a heterologous protein to FHA.

Advantageously the Bordetella strain has been made deficient in the production of toxins by elimination or deletion, at least partially, or by mutation, of the gene coding for the toxin so as to produce an inactive toxin. Such a gene may be particularly the gene coding for B. pertussis toxin or any protein having a structure or function similarity with such a toxin. It can be also the gene coding for hemolysin/adenylate cyclase toxin or the dermonecrotic toxin expressed by Bordetella strains or for proteins having structure or function similarities.

The Bordetella strain may be deficient in the production of one or various of these toxins.

Advantageously a heterologous protein consisting in a part of the hybrid protein comprises at least an epitope of a protein capable of being expressed by pathogens upon infections of the upper or lower respiratory tract.

Consequently said hybrid protein may comprise part of the protein FHA and part of the protein Sm28GST of Schistosoma masoni. This particular protein may be expressed into a strain of *B. pertussis* species and may be particularly the strain BPNX deposited under No. I-1770 on Oct. 8, 1996, in the national Collection of Microorganism Cultures of "l'Institut Pasteur", 28, Rue du Docteur Roux, F-75724, Paris, Cedex 15, France.

A strain according to the present invention may be obtained by elimination of the gene of the toxin from the genome of a virulent strain expressing said hybrid protein, or by partial deletion or by mutation so as to produce an inactive toxin.

Elimination may be carried out by any method known to those skilled in the art and particularly by crossing the virulent strain with a mobilizing strain, then by selecting, through markers adapted according to the strains, cells having lost the toxin gene. Such a loss of capacity of the virulent strain to express the toxin results from a double event of a homologous recombination between the virulent strain and a plasmid of the mobilizing strain. A person skilled in the art may refer for the obtaining of attenuated strains to the method described by Antoine and Locht (1990, Infect, Immun., 58, 1518–1526).

The characteristics of the deficient strains in the production of toxins, so selected, may be checked with various techniques, in particular by Western-blot.

The virulent strains expressing the hybrid protein may be obtained with the techniques known to those skilled in the art and, in particular, may be obtained as described in the above-mentioned French patent application FR-94 04 661 the contents of which are included into the present invention by reference. The recombinant DNAs comprising on the one hand a sequence coding for a heterologous peptide and on the other hand a sequence coding for a part of FHA are obtained through the methods known to those skilled in the art, in particular as described in Example V of the French patent application FR-94 04 661. This example results in the fusion of the region 190–211 of glutathion-S-transferase of 28 kDa (Sm28GST) of *Schistosoma mansoni*, with the truncated FHA protein. The recombinant DNAs coding for the hybrid proteins are selected, the sequence thereof is checked according to methods known to those skilled in the art, then transferred into Bordetella cells.

The person skilled in the art may refer for the implementation of the present invention to general manuals relating to these techniques and in particular to the following manual: Maniatis et al., 1982, Molecular Cloning: Laboratory Manual, Cold Spring Harbor Laboratory, Cold Spring Harbor N.Y., USA, or one of its recent re-editions.

It will be understood that the present inventions is not limited to *Bordetella pertussis* stains, but is applied to any Bordetella species, in particular these infectious for humans, including *B. parapertussis* or *B. bronchiseptica* or also to Bordetella strains infectious for animals, particularly the *Bordetella brotichiseptica* infectious for dogs or pigs or the *B. avium* strains for birds.

The heterologous protein, the sequence of which is included into the hybrid protein, may be any antigenic protein sequence, especially Bordetella, Shigella, Neisseria, Borrellia antigens, diphtheric, tetanic or choleric toxins or toxoids, viral antigens including hepatitis B, hepatitis C, polvovirus or HIV, or parasitic antigens such as these of Plasmodium, Schistosomas or be toxoplamas. It may be also include an epitope of a protein capable of being expressed by pathogens upon mucosal infections or systemic infections.

Such strains may be used for vaccination of humans or animals against various pathogens. They may be especially administrated intranasally.

Besides, the present invention relates to drugs and vaccines containing such strains or to pharmaceutical compositions containing a pharmacologically efficient quantity of such strains, and optionally one or more pharmacologically compatible excipients.

Another object of the present invention comprises the use of such strains to produce a drug or a vaccine for treating affections of the upper or lower respiratory tract, mucosal infections or systemic infections.

It is to be noticed that the strains according to the present invention have surprising activities. In fact, as shown in the following examples, the strains expressing hybrid proteins the toxin gene of which has been eliminated, induce a well higher production of antibodies than that obtained with the parent virulent strain, when both strains are administrated intranasally. The intranasal administration, for example by nasal spraying, allows the elimination of the contamination dangers associated with an injection through the skin and also avoids the destruction of vaccines administrated orally in the acidic environment of the stomach.

The present invention further relates to liposomes comprising at least one part of the FHA protein as well as at least a heterologous protein to FHA protein.

Such a heterologous protein may be a protein comprising the above-mentioned hybrid protein. It may thus comprise at least one epitope of a protein liable to be expressed upon infections of the upper or lower respiratory tract. Such liposomes may be obtained in a way known to those skilled in the art, for example with a process comprising the steps of mixing the FHA, the heterologous protein and lipids, then rehydrating the lipid film. They may be used for therapeutic uses to produce drugs and vaccines for stimulating the immune response against a given epitope.

The present invention thus relates to drugs containing such liposomes as well as pharmaceutical compositions containing pharmacologically efficient quantities of such liposomes as well as, optionally, pharmacologically compatible excipients.

The binding of the FHA with the liposome surface has the advantage of targeting towards the mucosal tissue the administration of the heterologous protein. The FHA will have thus two actions: on the one hand a targeting action of the liposomes due to a particular adherence property with respect to mucosal tissues and on the other hand immunostimulating properties will allow to increase the immune response against antigens of the heterologous protein.

This second property of the FHA is another object of the present invention.

Consequently, the present invention relates to the use of FHA to produce a drug for stimulating immune responses. Preferably, the FHA is associated with a heterologous molecule having an antigenic determinant or epitope, the action of which it will potentialize.

The present invention is illustrated but not limited in the following examples.

Wells 1 to 6 have been revealed with a FHA-specific antibody and wells 8 to 13 with a Sm28GST-specific antibody (190-211). The dimerized Sm28GST migrates differently in presence phospholipids. The presence of FHA has not modified the quantity of Sm28GST incorporated into the liposomes.

Figure 10A:
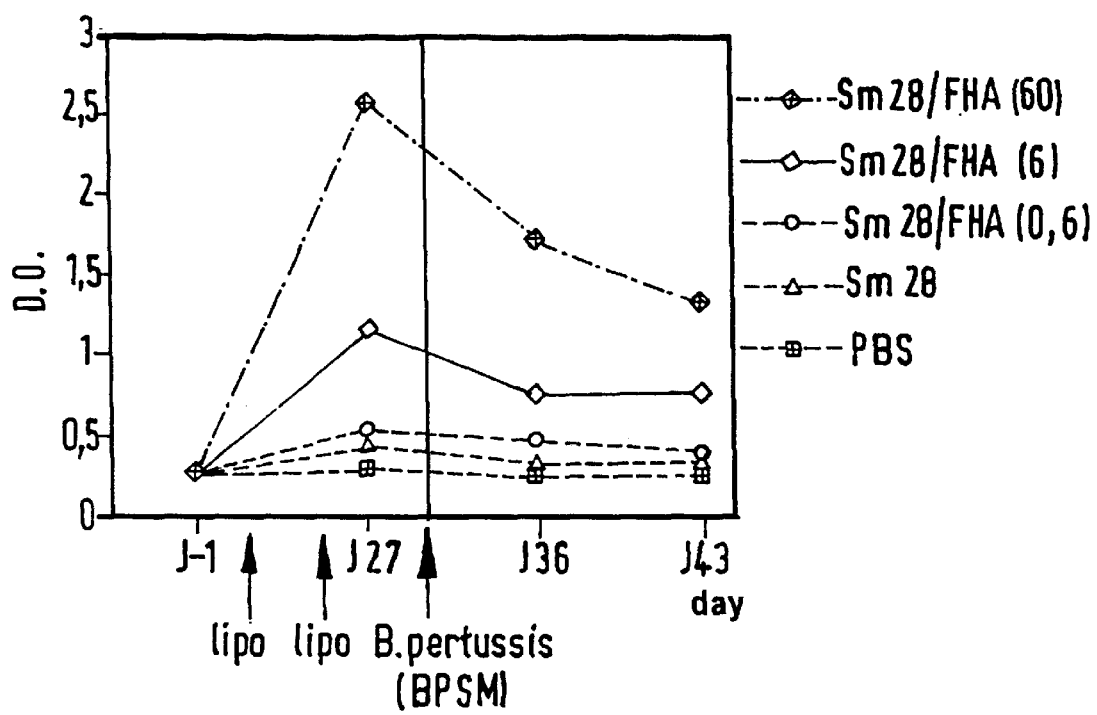
Figure 10B:
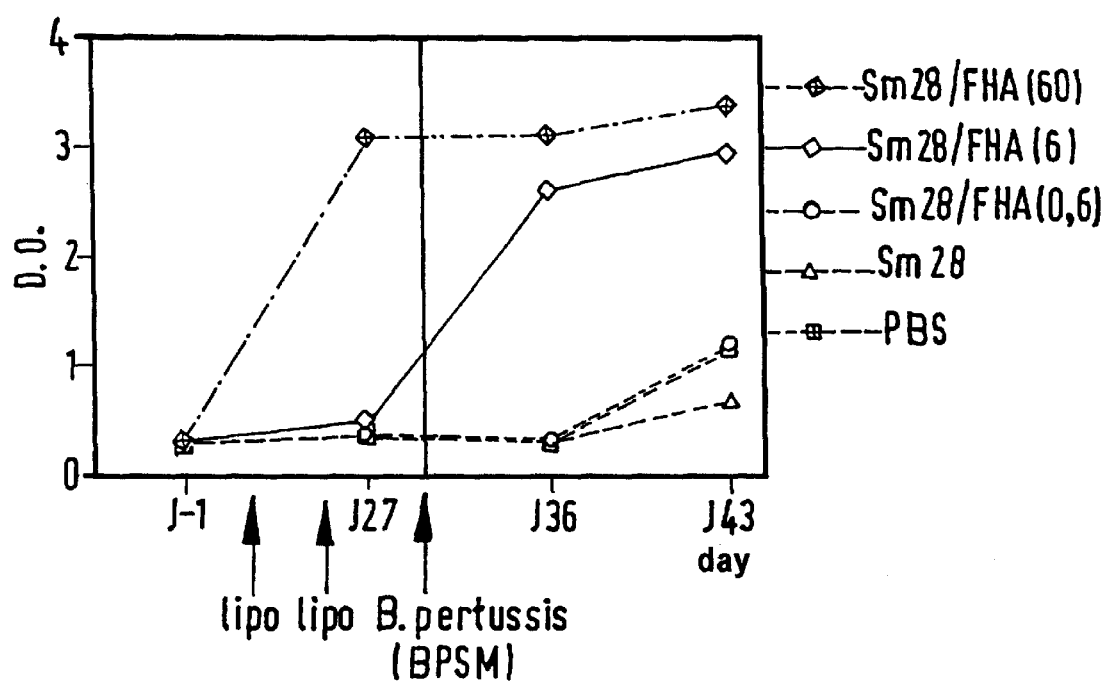

FIGS. 10A and 10B illustrate respectively the anti-Sm28GST and anti-FHA IgG(H+L) serum responses (serum pool 1/40 revelation 1 hour in ABTS). Two intranasal instillations at D1 and D14 have been carried out. Sera have been analyzed at D-1 and D27, and at D36 and D43 after an infection with B. pertussis which occurred at D28.

Figure 11A:
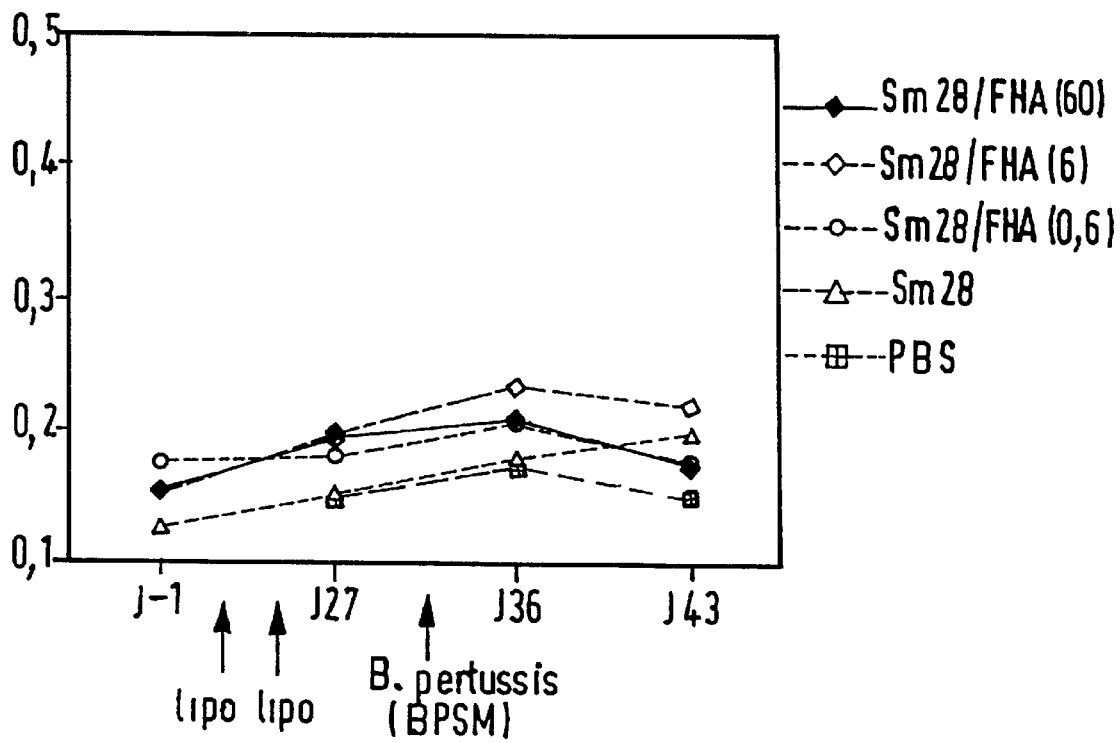
Figure 11B:
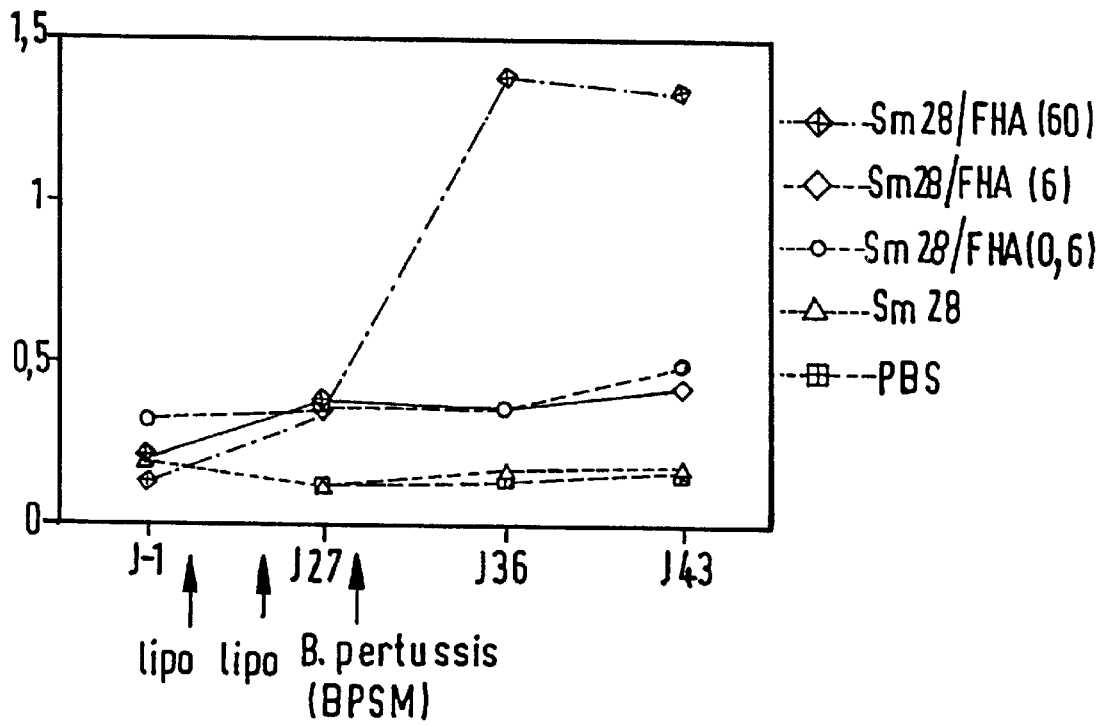

FIGS. 11A and 11B illustrate respectively anti-Sm28GST and anti-FHA IgA scrum responses (serum pool 1/40 revelation in OPD). Two intranasal instillations at D1 and D14 have been carried out. Sera have been analyzed at D-1 and D27, and at D36 and D43 after an infection with B. pertussis which occurred at D28.

EXAMPLES

Example 1

Protection Against an Infection by B. pertussis Previously Immunized with Different Strains Deficient in the Production of One or More Virulence Factors The wild strain of B. pertussis BPSM (Menozzi, F. D. et al., 1994, Infect. Immunol., 62, 769–778) has been as a reference for protection against a second infection with BPSM. The efficiency of the strain BPRA (Antoine R. et al., Infect. Immun., 58:1518–1526) deficient in the production of the pertussis toxin (PTX) has been compared with the strain BP347, having an insertion of the transposon Tn5 in the genome thereof leading to an incapacity to express the virulence factors such as PTX, adenylate-cyclase toxin (Ac-Hly), fimbriae, pertactin, and FHA (Weiss, A. A. et al., 1983, Infect. Immun., 42:33–41). A strain of Salmonella typhimurium aroA (Hoiset, S. K. et al., 1981, Nature 291:238–241) has been administered intranasally to a group of mice as an infection control by gram-negative bacteria. $5\times10^6$ B. pertussis bacteria in suspension in sterile PBS (scraped cells of a culture in solid medium, Bordet Gengou with sheep defibrinated blood (BG); Bordet, J. and Gengou, O., 1906, Ann. Institut Pasteur (Paris), 20:731–741) have been instillated nasally in a quantity of 25 μl per nostril to mice OF1 (impure strain, female mice 4 week old) under anaesthesia with pentobarbital. Bacteria S. typhimurium from a culture overnight at 37° C. in a liquid medium LB have been centrifugated during 10 min at 6000 revolutions per min and the deposit has been re-suspended in sterile PBS at a concentration of $2\times10^3$ bacteria/ml. The mice are then instillated with 50 μl of the bacterial solution. The lungs of three mice have been taken 3 hours after the injection, and then 7, 14, 21, 28 and 35 days after the injection. The lungs have been then homogenized in 5 ml of sterile PBS, then the bacteria have been counted 3 to 4 days after spreading the ground residues in solid medium BG containing 100 μg/ml of streptomycin and 25 μg/ml of nalidixic acid (BGSN). To simplify, the term "mouse X" has been used for "X-immunized mouse".

Figure 1A:
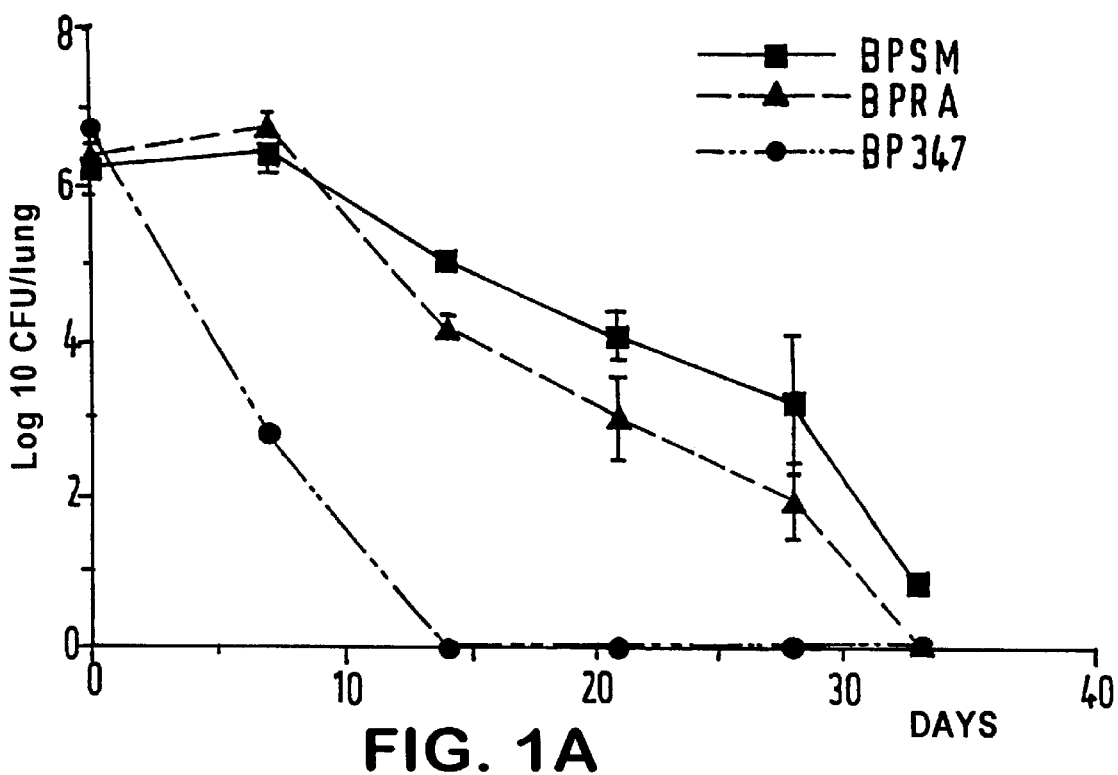
FIG. 1A illustrates colonization of lungs of mice OF1 by *B. pertussis* strains BPSM (PTX$^+$, FHA$^+$), BPRA (PTX$^-$, FHA$^+$) and BP347 (PT$^-$, FHA$^-$, PRN$^-$, Fim$^-$, AcHIy$^-$).

In a first period, the capacity for different attenuated strains of B. pertussis to colonize the respiratory tract of the mice has been checked. As shown in FIG. 1A, the number of bacteria BPRA increases in the lungs of the mice during the first seven days following the instillation, and then decreases during the four following weeks in the same way as the wild strain BPSM, but the elimination of the kinetics thereof is quicker. The strain BP347, deficient in the production of virulence factors, is unable to multiply during the first week and, 14 days after the immunization, no bacterium is found in the lungs. Finally, S. typhimurium, a microorganism colonizing the gastro-intestinal tract after an infection orally, is quickly eliminated, because it is unable to colonize the mucosas of the respiratory tract. A group of control mice has received intranasally 50 μl of sterile PBS.

Figure 1B:
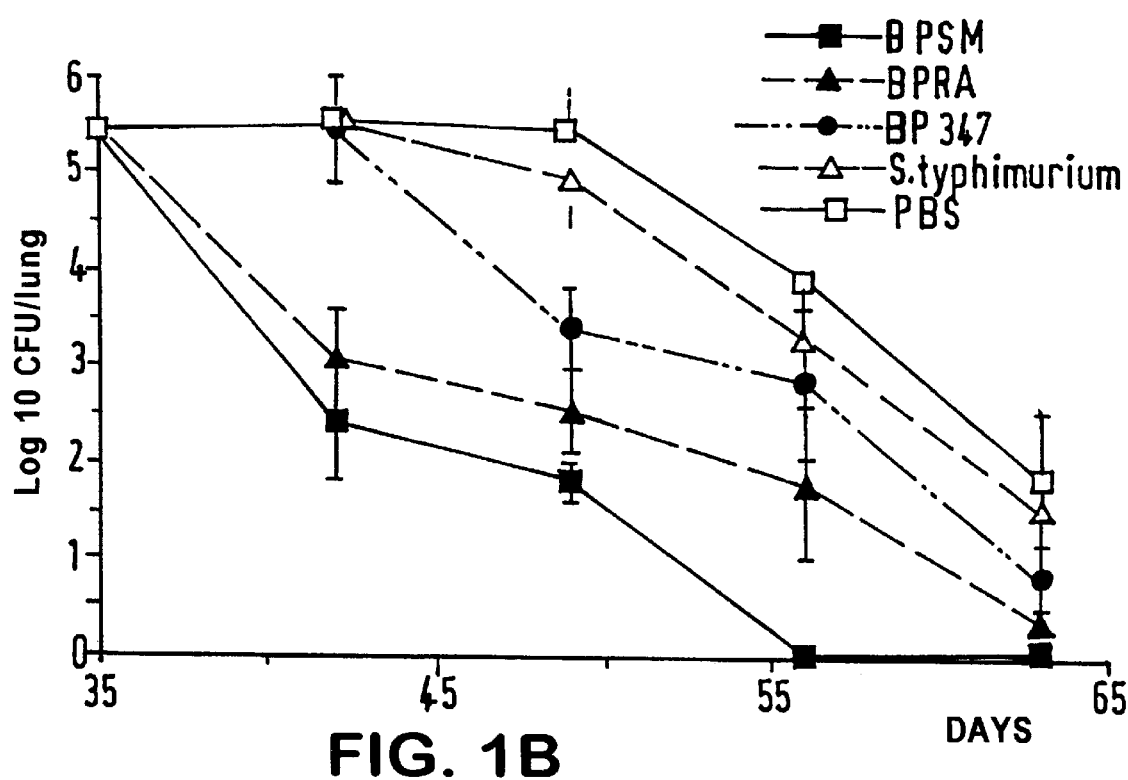
FIG. 1B illustrates colonization of lungs by bacteria BPSM of mice, previously immunized intranasally by the strains of FIG. 1A or by *S. typhimurium*. Three hours after the infection, three mice per group have been sacrificed and the viable number of *B. pertussis* estimated per lung. The other groups of mice have been analyzed one or more weeks after the infection as shown in the drawing. The bars represent the standard deviations on the average (SEM).
Figure 2A:
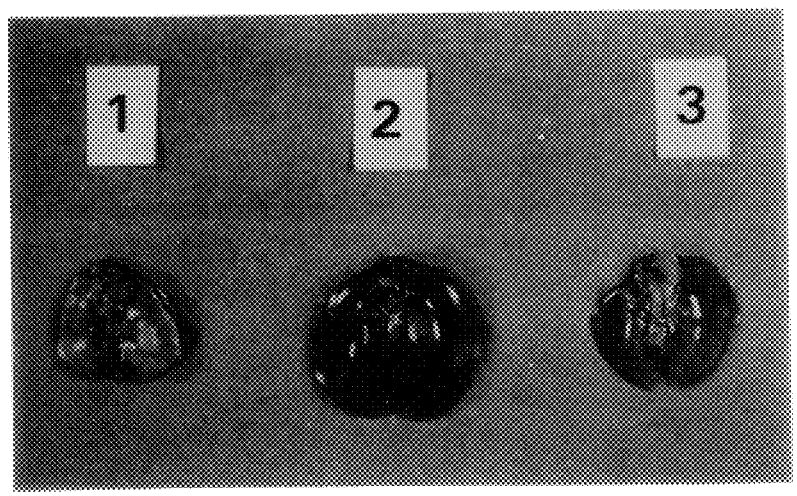
FIG. 2A represents lungs of healthy mice OF1 (1) and seven days after the nasal administration of $5\times10^6$ bacteria of the strains BPSM (2), BPRA (3).
Figure 2B:
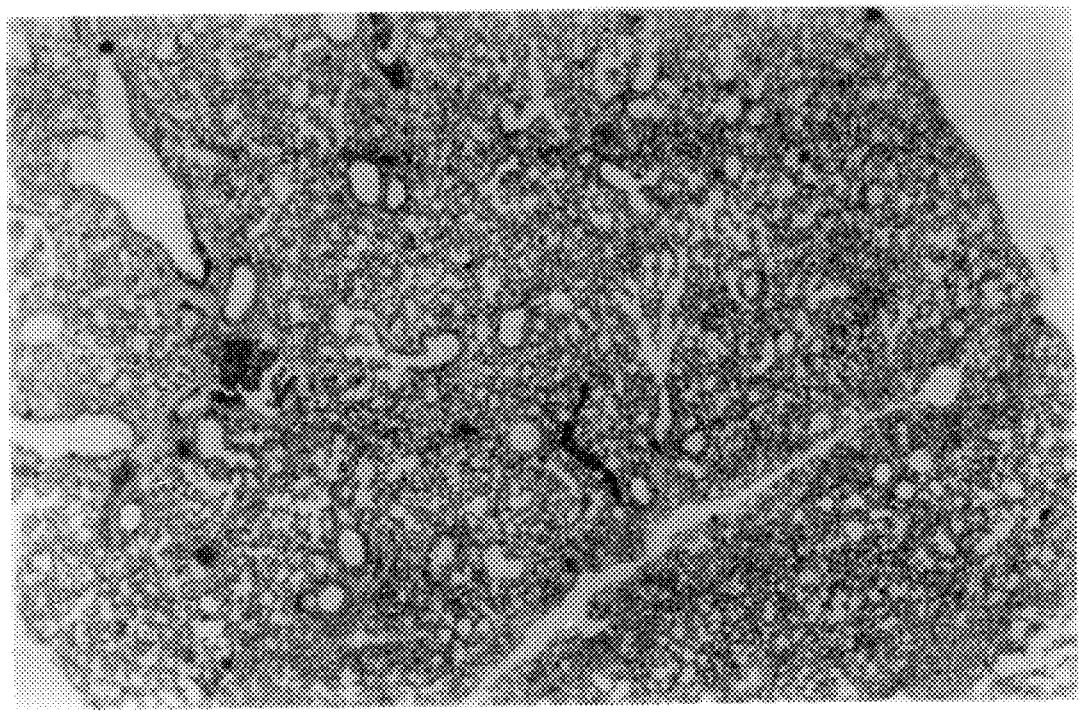
FIGS. 2B to 2D are sections of lungs 14 days after the intranasal administration of $5\times10^6$ bacteria of the strains BPSM (2C), BPRA(2D), the control corresponds to healthy mice (2B). The staining of the cell cores is obtained by hematoxyline treatment.
Figure 2C:
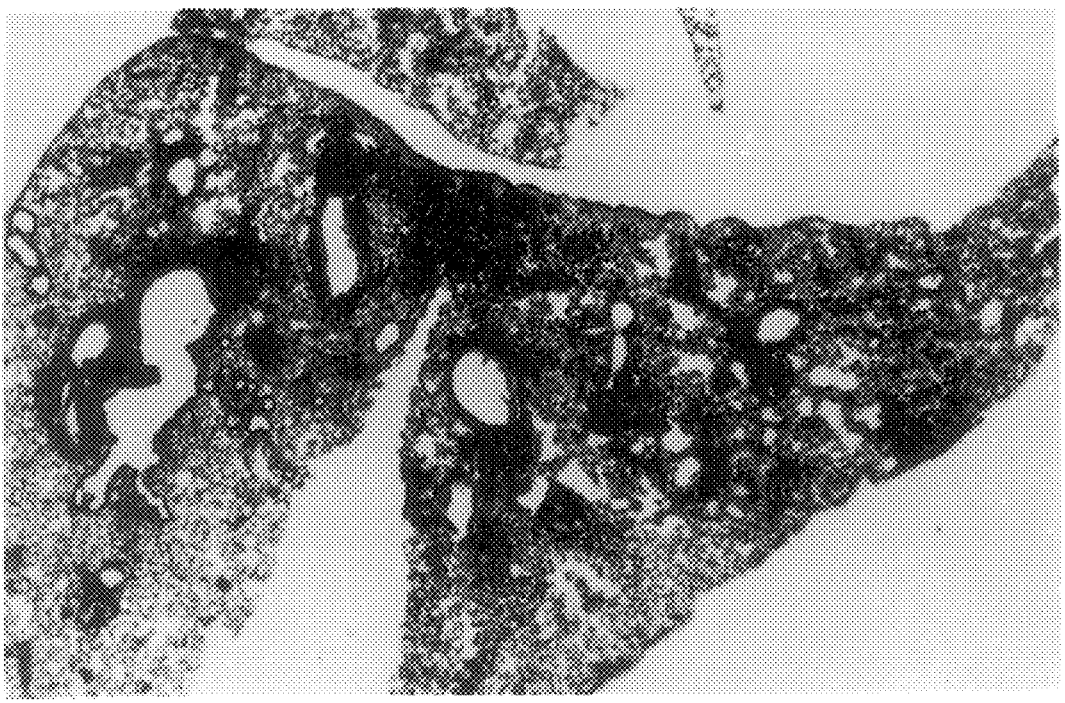
Figure 2D:
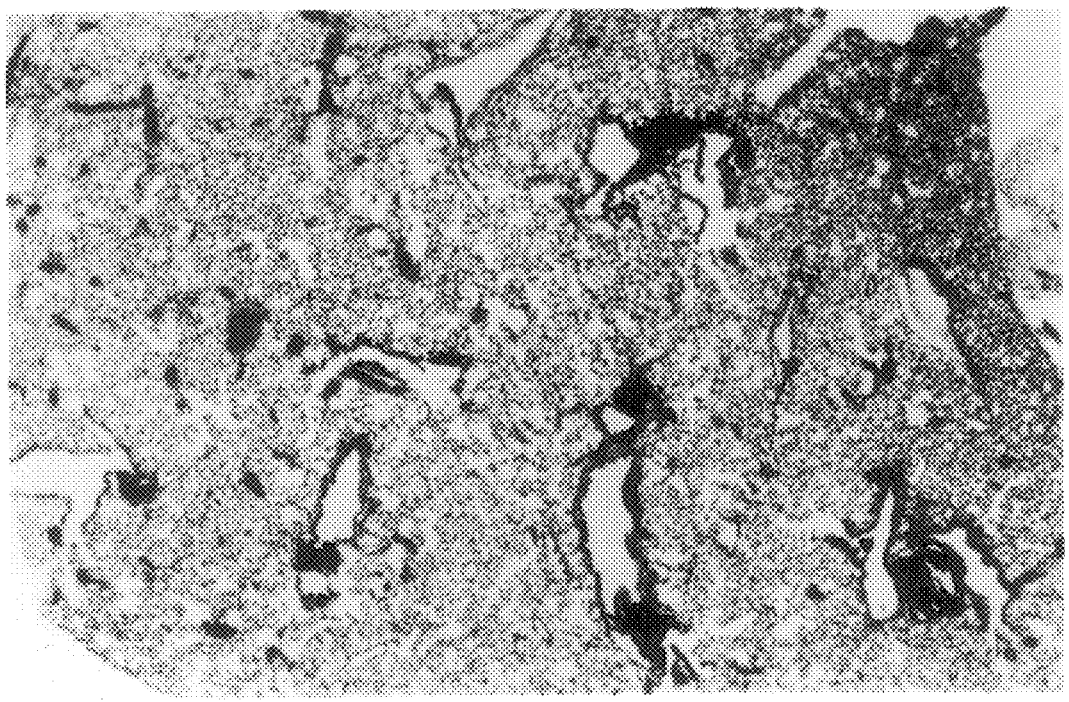
Figure 3:
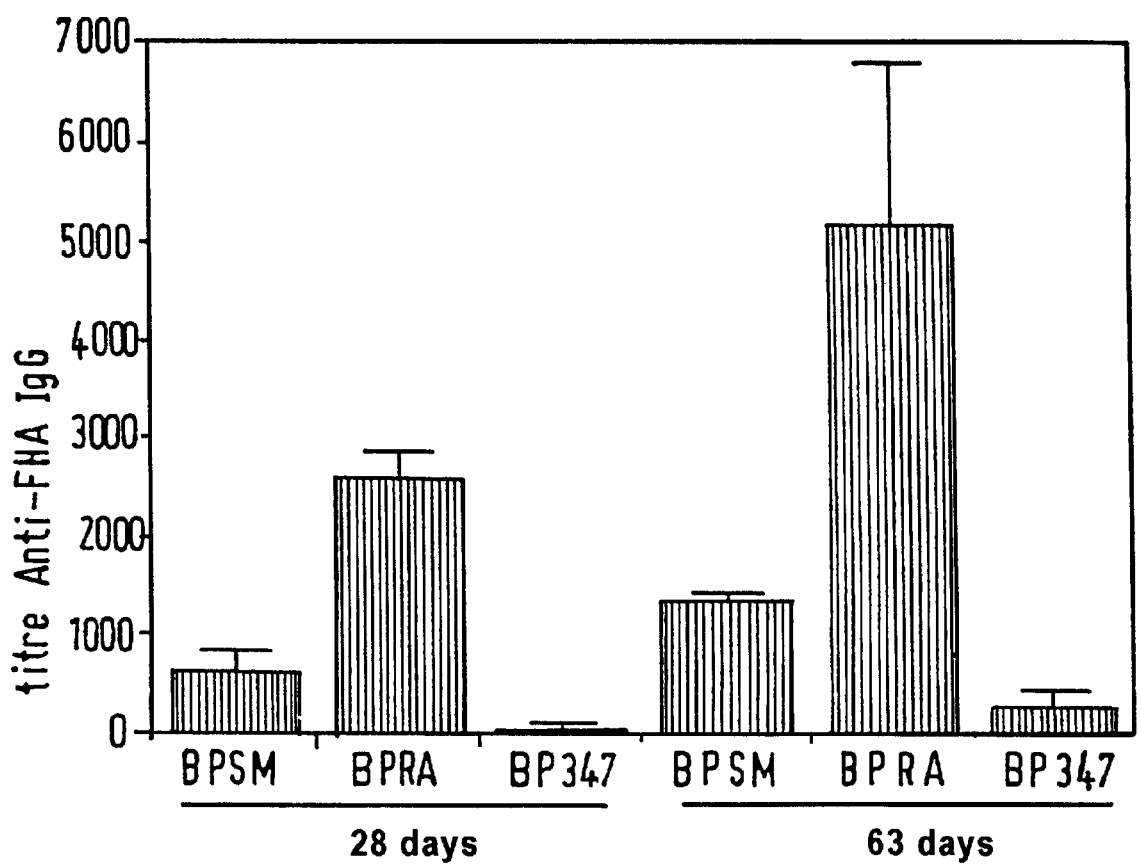
FIG. 3 illustrates the anti-FHA IgG response 28 days after the intranasal administration to mice OF1 of strains BPSM, BPRA and BP347, and 28 days after the second infection by BPSM (day 63). The estimation of the antibody rate has been determined through ELISA for three mice per group and per time.
Figure 4A:
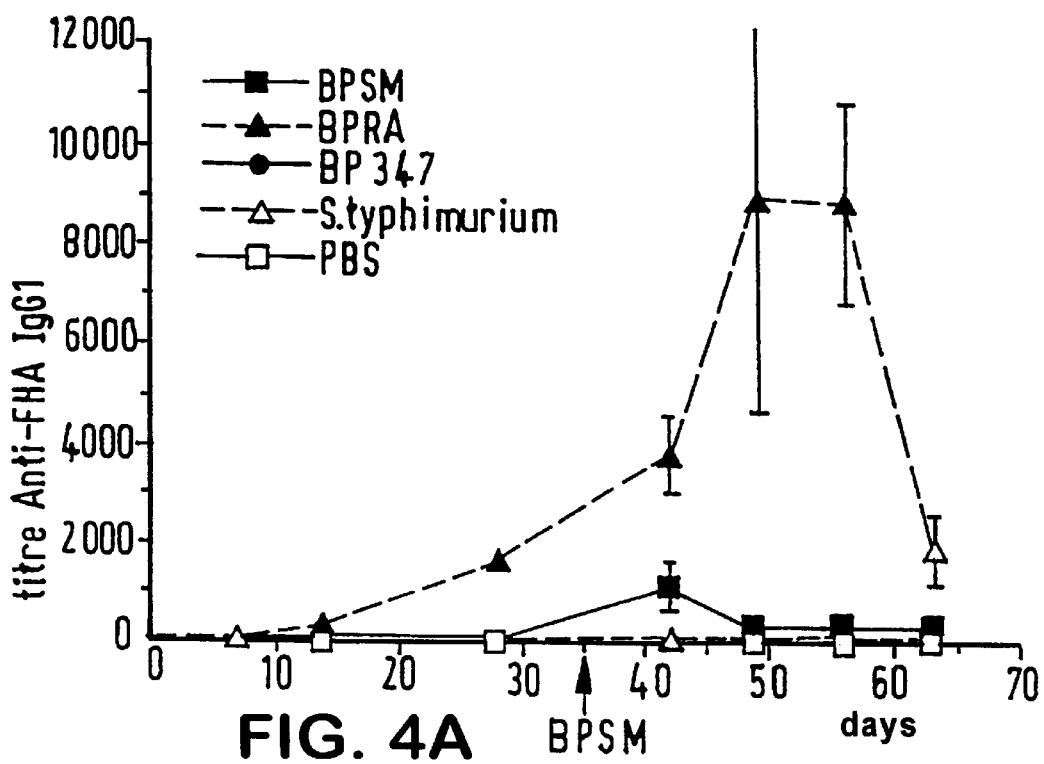
FIGS. 4A to 4D represent kinetics of the anti-FHA isotypical distribution. Sera of three mice per time have been analyzed for the presence of anti-FHA antibodies of isotype lgGI(4A), IgG2a(4B), IgG2b(4C) and IgA(4D) through ELISA technique.
Figure 4B:
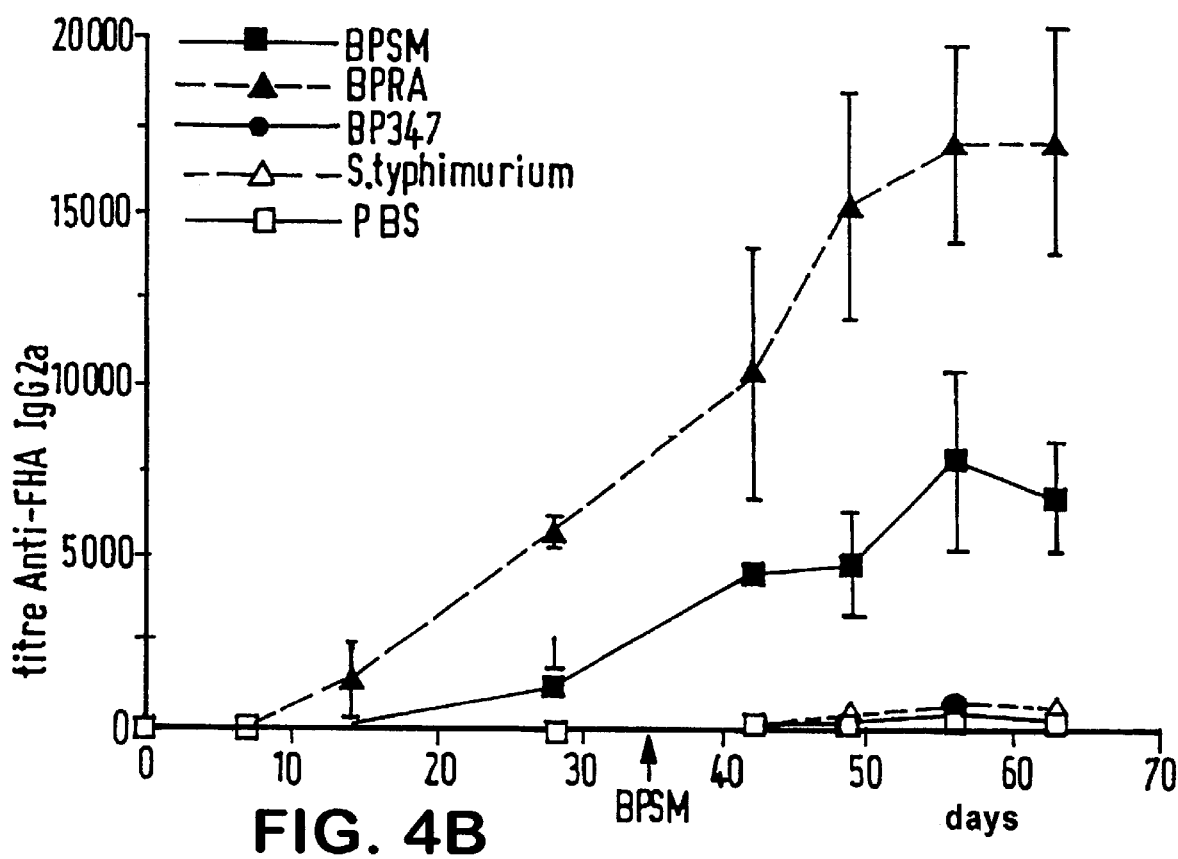
Figure 4C:
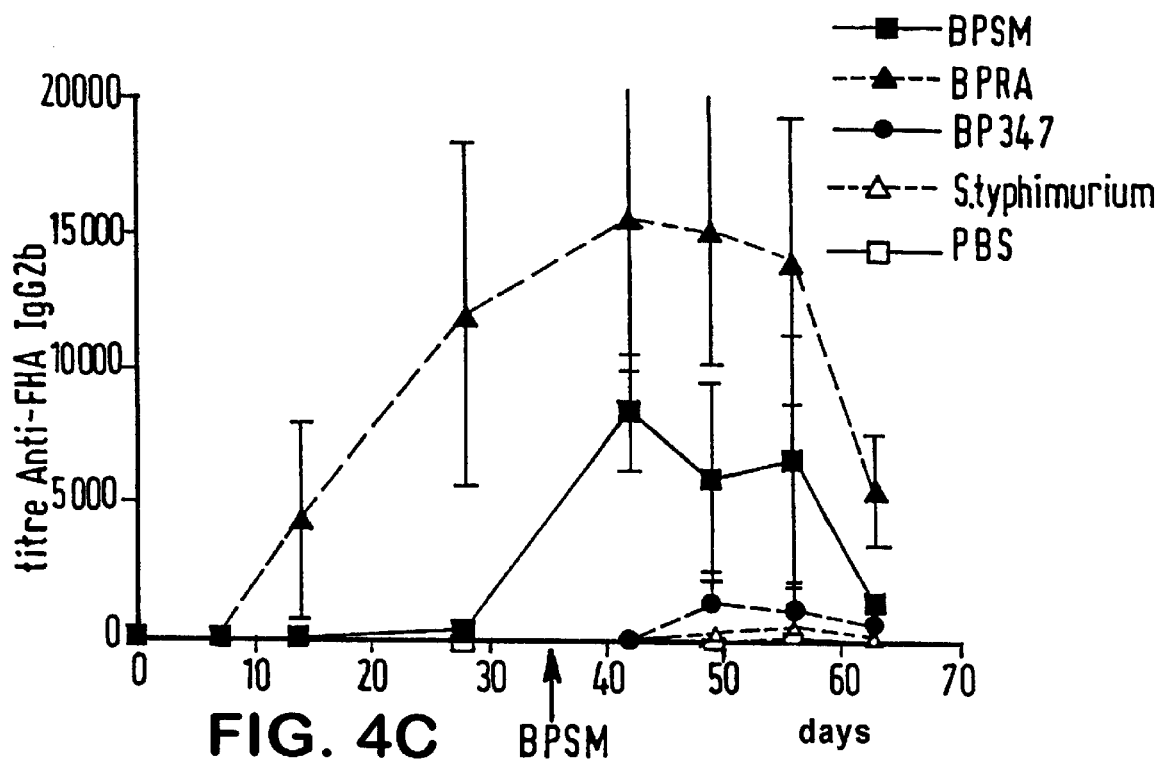
Figure 4D:
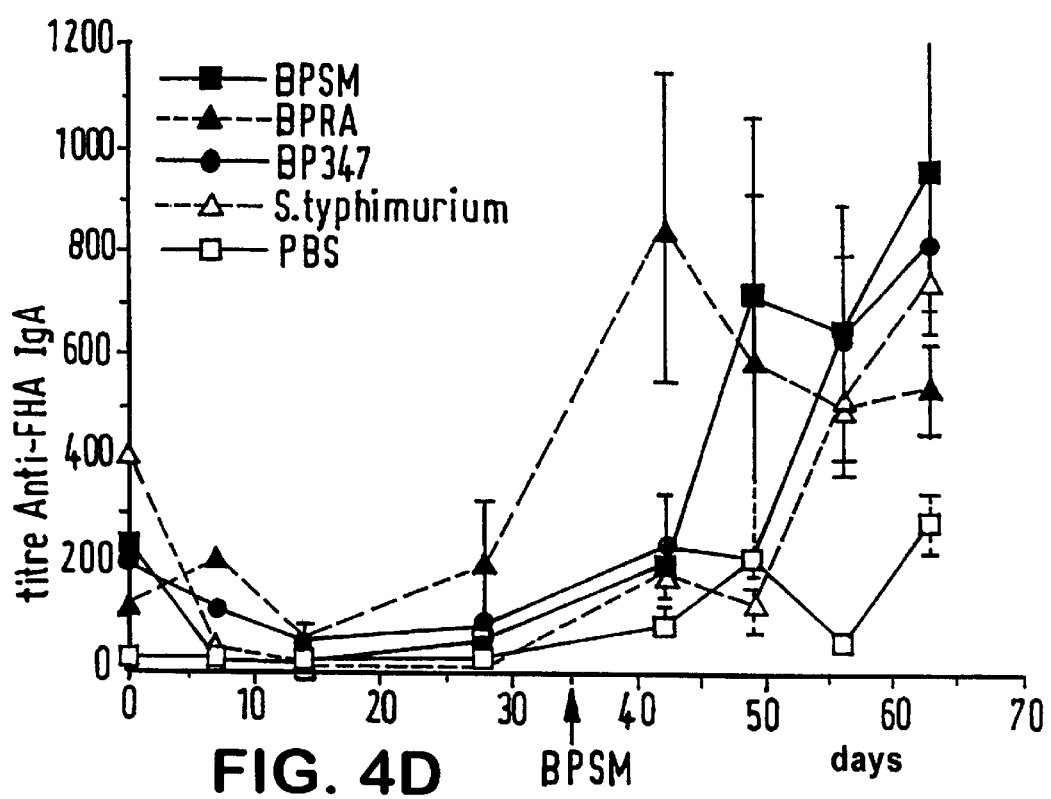
Figure 5A:
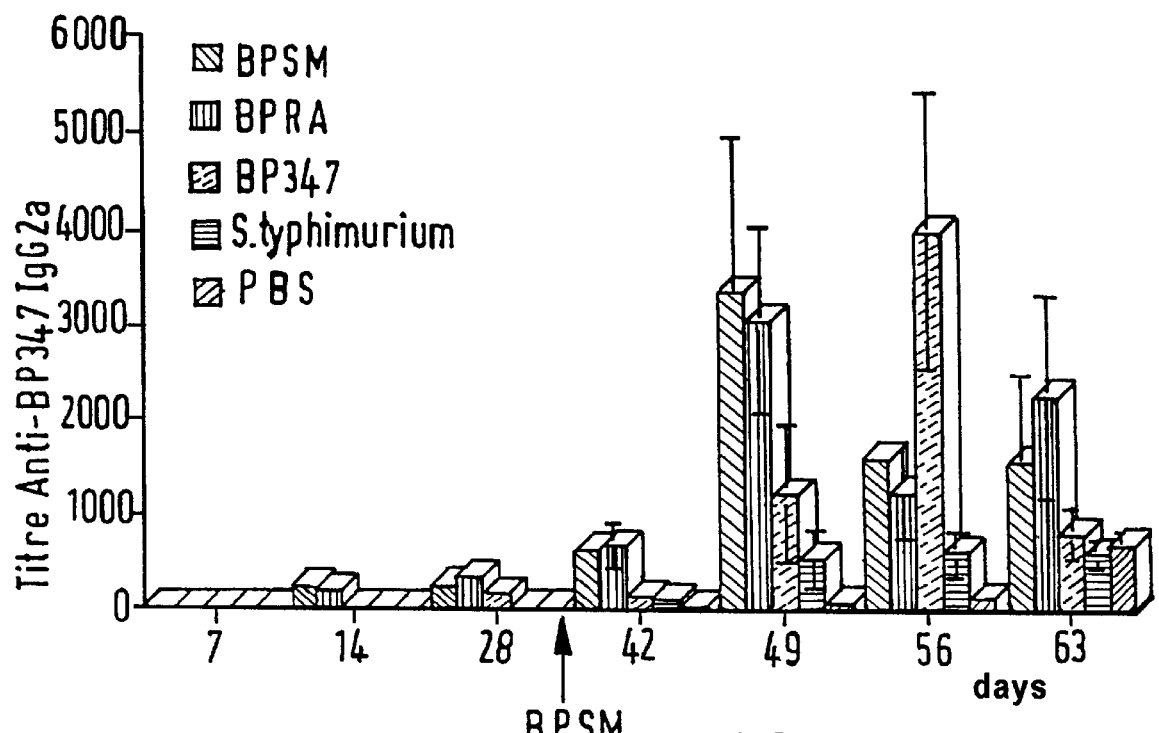
FIGS. 5A and 5B represent kinetics of the serum response IgG2A against B. pertussis antigenes. Sera of three mice per time have been analyzed for the presence of anti-BP347(5A) and anti-BPSM(5B) antibodies through ELISA technique.
Figure 5B:
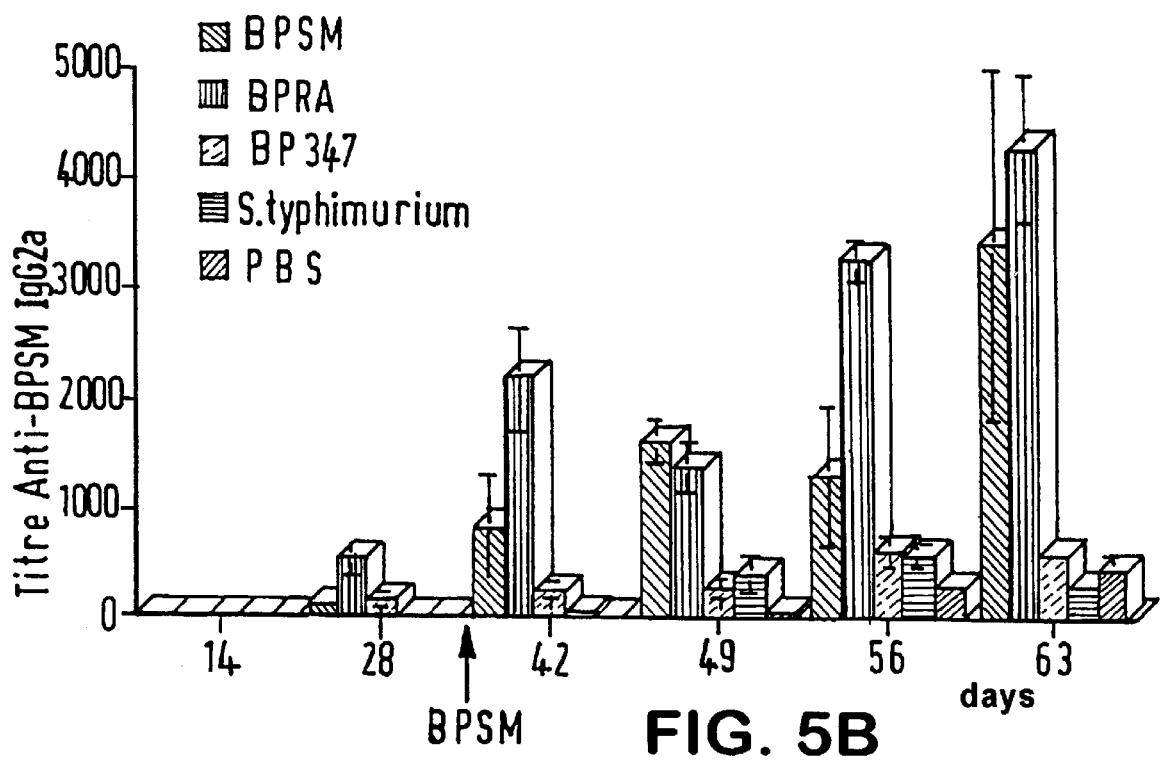
Figure 6:
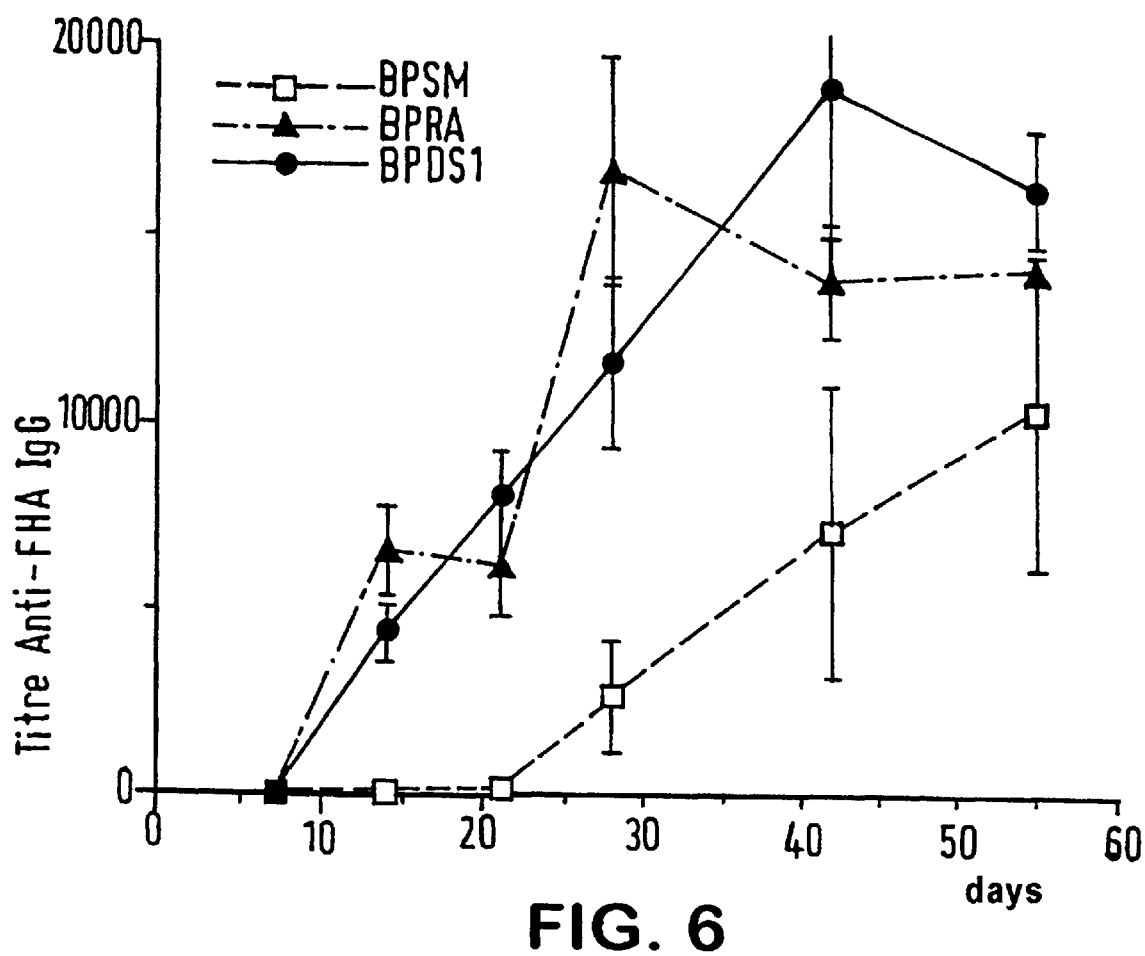
FIG. 6 represents kinetics of the anti-FHA serum response after the administration of the strains of B. pertussis BPSM (PTX$^+$), BPRA (PTX$^-$) and BPDS1 (S1–, oligomer B+). The antibody rates have been determined by ELISA for three mice per group and per time.
Figure 7:
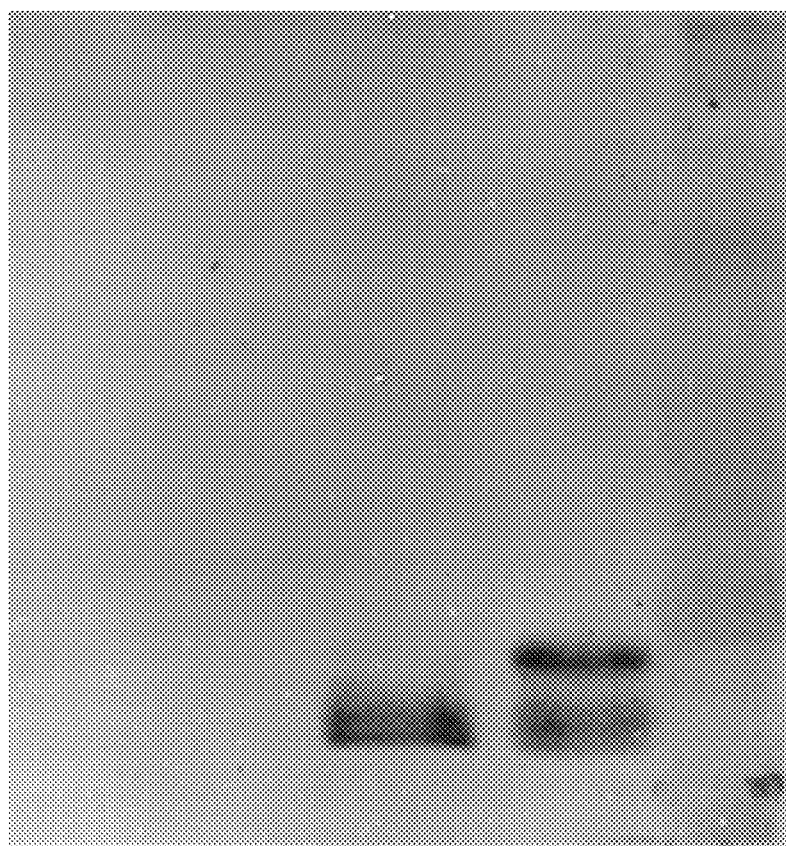
FIG. 7 represents the analysis by Western-blot of supernatants of cultures of non-recombinant strains BPSM (PTX') (well 4) and BPRA (PTX') (well 1) and recombinant strains expressing protein FHA-Sm28GST BPGR60 (PXT') (well 3) and BPNX (PTX') (well 2) by using the monoclonal antibody 1B7 directed against the sub-unit S1 of PTX. The well 5 corresponds to a molecular weight marker.
Figure 8:
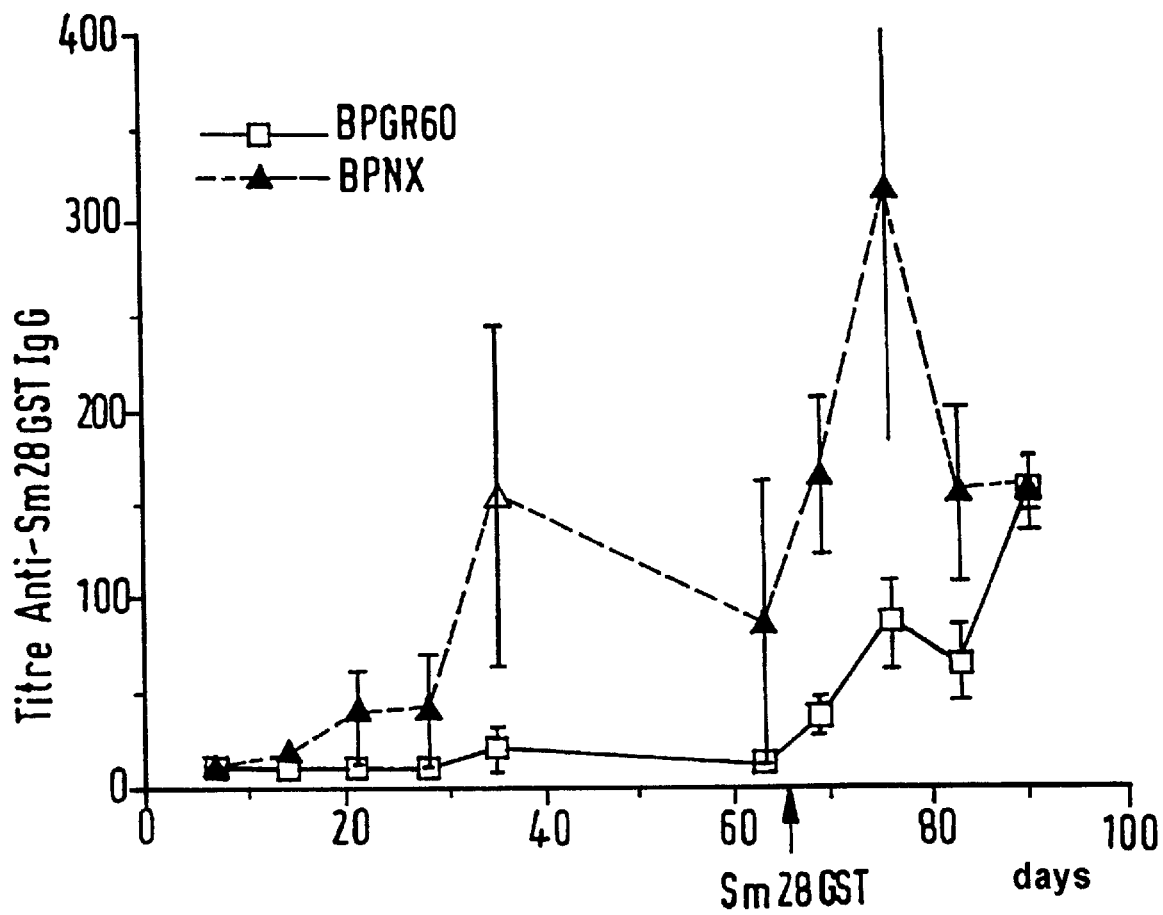
FIG. 8 represents kinetics of the anti-Sm28GST IgG serum response after an intranasal administration to mice OF1 of recombinant strains of B. pertussis BPGR6 (PTX') and BPNX (PTX').
Figure 9:
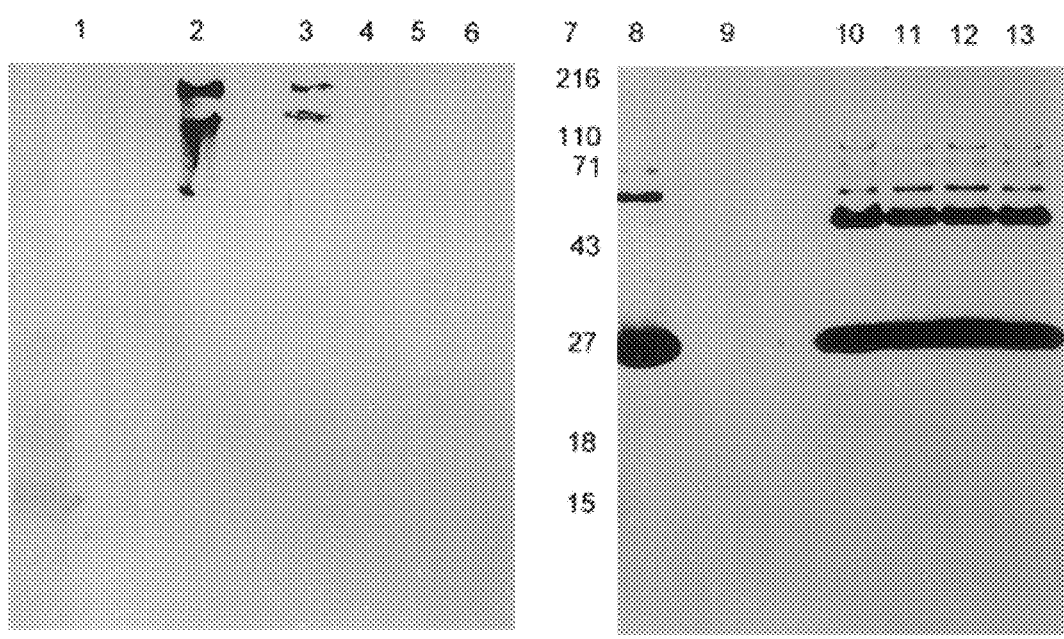
FIG. 9 is an immunotransfer (immunoblot) of various liposomic preparations (Sm28GST only in wells 6 et 13, Sm28GST with three different dosages of FHA, 60 μg/ml (wells 3 and 10), 6 μg/ml (wells 4 and 11) and 0.6 μg/ml (wells 5 and 12) analyzed after transfer of a SDS-PAGE gel on nitrocellulose. Wells 1 and 8 correspond to the Sm28GST non included in liposomes. Wells 2 and 9 correspond to the FHA non included in liposomes. Well 7 is the one of the molecular weight marker.

A second intranasal infection with the wild strain ($5\times10^6$ bacteria BPSM/50 μl of PBS) is carried out 35 days after the nasal immunization of mice with the different bacterial strains. The PBS control mice and the S. typhimurium mice show a similar colonization curve (FIG. 1B). In the BPSM and BPRA animals, the number of bacteria decreases rapidly after the second infection by BPSM. Seven days later, the quantity of bacteria present in the lungs of the BPRA mice is 300 times smaller than in PBS mice and is similar to the one observed in BPSM mice. On the contrary, during the first week following the infection, the BPSM bacteria seem to colonize the lungs of the BP347 mice in the same way as the lungs of the PBS mice. However, one week later, the BP347 animals present a reduced number of bacteria of about 100 times compared to the PBS group. 21 days after the second infection, no bacterium is detected in the lungs of the BPSM mice whereas a reduction of about 130 times for the BPRA mice and 12 times for the BP347 mice compared to the PBS mice is observed. 4 weeks after the infection, the almost total elimination of bacteria is reached in the BPRA mice whereas there are some remaining in the PB347 mice.

These results show that only the strain BPRA, deficient in the production of PTX, has in vivo a similar behaviour to the wild strain and that a prime infection by one of two strains protects against an efficient colonization of the respiratory mucosas by the wild strain.

Example 2

Histological Analysis of Inflammation at the Level of Lungs Induced by the Intranasal Administration of a *B. pertussis* Strain Deficient in the Production of *Pertussis* Toxin The mice are immunized with $5\times10^6$ bacteria (same immunization protocol as the one described in Example 1) from the wild strain BPSM or BPRA ($PTX^-$) strain. The number of bacteria being administrated is checked by taking lungs 3 hours after the intranasal administration and by counting bacteria after spreading lung ground residues. Seven days after the administration, the direct observation shows more voluminous and hemorrhagic lungs of BPSM mice compared to these of BPRA mice that only present some small hemorrhagic regions and have an identical volume to the one of the control mice (FIG. 2A).

To analyze the intensity of the cellular infiltration, lungs are taken 14 days after the administration of either of the *B. pertussis* strains. They are binded early upon their taking in 4% paraformaldehyde overnight at 4° C. After washing, the organs are dehydrated with successive ethanol (Merck) baths at increasing concentrations, and then contacted with 1-butanol (Merck) during 24 hours at 4° C. to improve paraffin infiltration. The inclusion is then carried out by paraffin infiltration (Paraplast Lancer) 4 to 5 hours at 56° C. Sections on lamellae of 6 μm thickness are made with a microtome. Previously to the marking, the sections are deparaffined with toluene (Merck) and re-hydrated. Re-hydration of the sections, carried out by alcohol baths in decreasing concentrations, is terminated by a buffer bath TBS (Tris HCl 10 mM, NaCl 150 mM, pH 7,4). Staining of the cell cores is carried out by contact during 10 min with hematoxyline, followed by rinsing the lamellae during 10 min with tap water. Photographs of the sections are made with an objective×10. A cellular infiltration is observed at the level of the lungs both in BPSM and BPRA mice, the lungs of a healthy mouse being used as a negative control (FIG. 2B). However, whereas the cellular infiltration is slight and limited to the periphery of the upper tract for the BPRA mice (FIG. 2D), it seems to be massive and has reached up to the lung alveoles for the BPSM mice (FIG. 2C).

These observations show that the BPRA strain deficient in the production of PTX induces a well weaker inflammatory reaction at lung level than that due to a nasal administration of BPSM wild strain.

Example 3

Analysis of Anti-FHA Serum Immune Response After an Intranasal Administration of the Various Bacterial Strains The titers of the total anti-FHA IgG response are determined in mouse serum 28 days after the intranasal administration of the strains of *B. pertussis* (BPSM, BPRA, BP347) as well as one month after a second infection with BPSM (same protocol as described in Example 1). The mice are bled by needle puncture at the level of retroorbital plexus and sera are preserved at −20° C. up to their analysis by ELISA technique.

During the period 28–63 days, the titers of the anti-FHA IgG response have doubled in each mouse group immunized with the different *B. pertussis* strains (FIG. 3). Interestingly, BPRA mice present an anti-FHA response four times superior than the one observed in BPSM mice, said difference being observed 28 days after immunization or after the second infection with BPSM. These results are found indistinctly when ELISA tests are effected against FHA purified from BPSM or BPRA strain.

To determine if the differences in the anti-FHA serum response of BPSM and BPRA mice were only quantitative and/or qualitative, a profile of the anti-FHA response has been performed by ELISA.

The analysis of specific response kinetics shows 14 days after the intrasanal administration the presence of IgG1 (FIG. 4A), IgG2a (FIG. 4B) and IgG2b (FIG. 4C) in the serum of BPRA mice, whereas IgG2a and IgG2b are detected in BPSM mice only one month after immunization. In these two groups of mice, the second infection by BPSM has induced an increase of the anti-FHA IgG2a and IgG2b response. On the other hand, whereas a great increase of the specific IgG1 response is observed in BPRA mice, a small transient production is detected in BPSM mice one week after the second infection. One month after this infection, a reduction of the IgG1 and IgG2b rate is detected in the serum of BPRA mice whereas the IgG2a rate remains stable. The analysis of the anti-FHA IgA serum response shows one week after the second infection by BPSM a high production of specific IgA in the serum of BPSM mice (FIG. 4D). One week later, such a serum IgA level is reached in BPRA mice, followed 7 days later by the detection of anti-FHA IgA in the serum of BP347 mice and *S. typhimurium* mice.

These distribution kinetics for the anti-FHA isotypical response put then in evidence an earlier and higher specific serum response in the serum of BPRA ($PTX^-$) mice compared with the one found in BPSM ($PTX^+$) mice.

One of the hypotheses which could explain those results would be that the FHA quantity expressed at the surface and/or secreted by the BPRA strain is superior to the one produced by the BPSM wild strain. An immunoblot analysis with an anti-FHA rat polyclonal antibody has been effected on culture supernatants and cellular lysates from a liquid culture of various *B. pertussis* strains in a Stainer-Scholte medium (Stainer, D. W. and Scholte, M. J. 1971, J. Gen. Microbiol. 63:211–220) containing 1 g/l of 2,6-O-dimethyl-β-cyclodextrine (Imaizumi, A. et al., 1983, Infect. Immun. 41:1138–1143). This study has put in evidence similar quantities of FHA produced by BPRA and BPSM strain.

A potentially immunoregulatory activity for PTX, which would act as an immunosuppressor element, could be at the origin of the weak intensity of the anti-FHA response in BPSM ($PTX^+$) mice compared with the one obtained with BPRA ($PTX^-$) mice. A study of the IgG2a response, more sensitive than the total IgG response, against the total antigens of BP347 and BPSM bacteria has been carried out on sera of each group of mice. To prepare total antigens, bacteria have been striated on BGS boxes, then after a 48 h culture, suspended again at a concentration of 2, $5\times10^9$ bacteria/ml in PBS containing 0.5 mM PMSF and 1 mM EDTA. The cell suspension is then lysed with two successive passes in a French press. The antibody rates directed against antigens of BP347 strain (antibody anti-BP347) are similar in sera of BPSM and BPRA mice (FIG. 5A) whereas slight differences are noticed concerning the levels of the anti-BPSM response with a higher response in BPRA mice probably linked to the anti-FHA IgG2a rate (FIG. 5B). Moreover, whereas the level of anti-BP347 antibodies decreases progressively in the serum of BPSM and BPRA mice, the anti-BPSM IgG2a response continues on increasing at least up to 28 days after the second infection by BPSM, namely in parallel with the anti-FHA IgG2a response.

Example 4
Study of the Part Played by the Enzymatic Activity of PTX on the Anti-FHA Serum Response PTX is an oligomeric protein comprising 5 sub-units so-called S1 to S5. This holotoxin has an A-B type structure where A corresponds to the sub-unit S1 expressing the enzymatic activity ADP-ribosyltransferase and NAD-glycohydrolase (Kataka. T. et al., 1983, Arch. Biochem. Biophys., 224:590–298). This protein has two cysteines which form a disulfide bridge when the toxin is secreted by the bacterium. One of these cysteines (cys-41) is located near the NAD binding site on the enzym (Locht, C. et al., 1990, J. Biol. Chem. 265:4552–4559) and is essential for stability of *B. pertussis* S1 sub-unit. To determine the part played by the PTX enzymatic activity on the anti-FHA response, a group of mice has received $5\times10^6$ bacteria of a *B. pertussis* strain containing the gene coding for the toxin integrated into the chromosome and called BPRA(pPT2) or BPDS1, where the cys-41 residue of S1 has been deleted (Antoine, R. et al., 1990, Infect. Immun. 58:1518–1526). The sub-unit S1 is not detectable in the culture supernatant of such a strain, but the oligomer B, a component which allows a binding with the target cells, may be assembled and secreted. The capacity of BPDS1 strain for colonizing the respiratory tract of mice as well as the cellular infiltration observed at the lung level 14 days after the administration is identical to the one of the BPRA strain. The kinetics of the anti-FHA scrum response after the administration of the BPDS1 strain intranasally ($5\times10^6$ bacterial/50 $\mu$l PBS) has been analyzed over two months. The anti-FHA IgG antibodies observed rate of the BPDS1 mice is similar to the one of the BPRA mice and higher than the one detected in the serum of BPSM mice (FIG. 6).

These results show that the PTX enzymatic activity is involved in the reduction of the serum response against the major adhesine of *B. pertussis, the FHA.*

Example 5

Chromosomic Construction of a Recombinant Strain Deficient in the Production of *B. pertussis* Toxin (BPNX) Expressing a Modified Protein Sm28GST of *S. mansoni*

An attenuated recombinant strain of *B. pertussis* has been constructed so as to verify the correlation between the chromosomic deletion of the gene coding for PTX and the increase of the serum antibody response directed against a heterologous antigen fused with the FHA after an intranasal administration of such attenuated recombinant strain. The model heterologous antigen is a glutathion S-transferase of 28 kDa of *Schistosoma mansoni* (Sm28GST) (Balloul, J. M. et al., 1987, Nature (London), 326:149–153).

To eliminate the PTX gene from the genome of the virulent strain BPGR60 ($Sm^R$, $Gen^S$, $Nal^R$) of *B. pertussis* expressing a modified Sm28GST of *S. mansoni* fused with the FHA (Renault-Mongénie, G. et al., 1996, Proc. Nati. Acad. Sci. USA, 93:7944–7949), this latter is crossed on a solid medium BG with the mobilizing strain *E. coli* S17-I (pRIT13295) ($Sm^S$, $Gen^R$, $Nal^S$), the plasmid pRIT13295 having the flanking regions 5' and 3' of the PTX gene (Antoine, Locht, 1990, Infect. Immun. 58:1518–1526). The homologous double recombination events occur at the level of the flanking regions of this gene. After conjugation, the bacteria having experienced both recombination events are selected on selective media as described previously (Antoine and Locht, 1990, Infect. Immun., 58:1518–1526).

The preservation of antigenicity of the fusion protein FHA-Sm28GST and the loss of capacity of the BPNX attenuated recombinant strain for expressing the PTX are checked by Western-blot after separation of the protein fraction from the culture supernatant and the one associated with the cells by SDS-PAGE on a 10% gel. The recognition of the fusion protein is carried out by using polyclonal antibodies of rats directed against the FHA and polyclonal antibodies of rats directed against the peptide 190–211 of the Sm28GST. The toxin is identified in the culture supernatants of the strains BPSM and BPGR60 through a monoclonal antibody of mice 1B7 directed against S1 (Sato et al., Infect. Immun., 46, 422–428, 1984) whereas it is not detected in the supernatants of the strains BPRA and BPNX (FIG. 7).

The strain BPNX has been deposited on Oct. $8^{th}$ 1996 in CNCM under the No. I-1770.

Example 6

Immunogenicity of the Recombinant Strain BPNX

The colonization of the recombinant strain BPNX in mice OF1 has been checked (as already described for strain BPRA in example 1) and shows a colonization kinetics for the lungs identical to the one of the wild strain of *B. pertussis.*

The intensity of IgG anti-Sm28GST serum response obtained with mice having received $5\times10^6$ bacteria/50 $\mu$l intranasally of the strain BPNX is compared to the one obtained after the administration of the strain BPGR60. A restimulation of the mice is carried out, two month after the immunization with the recombinant strains of *B. pertussis*, by intranasal administration of 20 $\mu$g recombinant antigene (rSm28GST produced by *E. coli*) in PBS. The kinetics of the serum immune response is effected on groups of 3 to 5 mice for each time.

Whereas no serum response specific to the Sm28GST is obtained after a nasal administration of the virulent recombining strain BPGR60, anti-Sm28GST IgGs are detected already on the $14^{th}$ day following the administration of the attenuated recombinant strain BPNX and the production thereof increases continuously up to 35 days after the administration (FIG. 8). Two months after the imnmunization, a slight reduction of this anti-Sm28GST serum antibody rate is observed in BPNX mice whereas such a response is not detected in BPGR60 mice. In the weeks following the re-vaccination with the rSm28GST, a production of anti-Sm28GST antibodies is put in evidence in BPGR60 mice, but it remains weaker than the one obtained in BPNX mice.

Thus, these results show a correlation between the chromosomic deletion of the gene coding for PTX and the increase of the serum antibody response directed against an heterologous antigen fused with the FHA. With quantities of bacteria being similar, only one intranasal administration of an attenuated recombinant strain of *B. pertussis* allows to induce a specific serum response of the heterologous antigene fused with the FHA, whereas a re-vaccination was necessary with the virulent recombinant strain.

Example 7

Production of Lisopomes Containing an Antigen of Interest Having the FHA in Surface The antigen used is the glutathion S-transferase enzyme of *S. mansoni*, a protein of 28 kD, which induces a protective immunity in mammals by reducing the number of adult worms and decreasing the fertility of these worms. The Sm28GST model has been used as antigen of interest to improve such liposomes.

The principle is to bind the FHA, the major adhesine of B. pertussis which has at least three activities of binding with various cell types at the liposome surface so that these latter adhere to the mucosas through them. The results obtained show that the presence of FHA at the liposome surface containing Sm28GST induces a dosage effect on the specific serum response of the Sm28GST. Such effect should be due to the fact that the presence of this *B. pertussis* adhesine at the liposome surface leads to an increase of the number of particles reaching the inductor sites. On the other hand, an homogenization of the specific serum response is observed after the administration of such liposomes Sm28GST/FHA.

Liposomes DPPC/DMPG (dipalmitoylphosphatidylcholine:dimiristoylphosphatidylglycerol) in a ratio 9/1 being formed by hydration of dry preparations (Phillips, N. et al., 1996, Vaccine, 14:898–904) have been used. The FHA has been purified from culture supernatants of *B. pertussis* (strain BPRA) through passing on an heparin column. It has been checked that the properties observed were not due to the presence of endotoxins in that preparation. Mice OF1 (outbred) of which the genetic heterogeneity is the most representative of what can be observed in a human population have been used.

Administration of liposomes DPPC/DMPG containing Sm28GST to mice OF1 has led to a specific serous and secretory immune response of the Sm28GST.

In order to observe an improved effect of the immune response due to the use of FHA at the liposome surface, the sub-limit conditions to obtain an immune response with liposomes Sm28GST have been determined. A nasal instillation at 15 day intervals of liposomes produced with different dosages of Sm28GST (5 mg/ml, 1 mg/ml, 0.2 mg/ml) for a quantity of 2 $\mu$M phospholipides per animal and per injection has shown that a quantity of 1 mg/ml gave a weak, but detectable immune response.

The conditions for producing the liposomes, which allow to obtain the presence of FHA at the surface have also been determined. FHA has hydrophobic sequences which should allow it to be inserted easily into the liposomes. However, the addition of FHA to already produced liposomes Sm28GST has not given satisfactory results. On the contrary, when FHA has been added to the Sm28GST solution to rehydrate the lipid film and produce liposomes, mixed liposomes have been able to be produced. The presence of FHA and Sm28GST at the liposome surface has been visualized by using either a polyclonal antibody against FHA or a polyclonal antibody against Sm28GST.

Example 8

Increase of the Immune Response with the FHA Quantity

Mice OF1 have been immunized with two instillations at 15 day intervals (5 groups containing about fifteen animals each). A control group has been immunized with PBS, one group has been immunized with liposomes produced with 1 mg/ml Sm28GST. The three other groups comprised liposomes produced with 1 mg/ml Sm28GST and respectively 0.6 $\mu$g/ml, 6 $\mu$g/ml and 60 $\mu$g/ml FHA. It has been checked by Western-blot after separation of the liposomic preparation by SDS-PAGE by using a 12% gel, that the quantity of Sm28GST incorporated into the liposome was identical in the resolution limits of the technique in the absence or in presence of any quantity of FHA in the beginning solution. The protein recognition is carried out by using polyclonal antibodies of rats directed against FHA and polyclonal antibodies of rats directed against the peptide 190-211 of Sm28GST (FIG. 9).

The mice have been bled 2 weeks after the last injection. The analysis of the serum pools has evidenced an increase of the anti-Sm28GST IgG(H+L) response depending directly from the quantity of FHA being used (FIG. 10). The anti-FHA IgG(H+L) response has only been detected in the group comprising the highest dosage of FHA (FIG. 10).

The analysis of individual sera has shown an homogenization of the response in the group comprising a high dosage of FHA (Table). The analysis of the obtained isotypes has evidenced a mixed response: (presence of IgG1, IgG2a and IgG2b). The curves obtained have the same profile as the curve IgG(H+L) both for Sm28GST and FHA. A mixed response has also been obtained for liposomes containing only Sm28GST. No response polarization effect has been observed.

TABLE

Analysis of the anti-Sm28GST IgG(H + L) response of individual sera at D27

| Type of liposomes | Positive mice Sm28GST | Positive mice FHA |
|---|---|---|
| A:Sm28GST/FHA(60) | 16/16 | 16/16 |
| B:Sm28GST/FHA(6) | 10/16 | 1/16 |
| C:Sm28GST/FHA(0,6) | 5/15 | 0/15 |
| D:Sm28GST | 5/15 | 0/15 |
| E:PBS | control | control |

What is claimed is:

1. *Bordetella pertussis* strain BPNX deposited under accession number I-1770 on Oct. 8, 1996, in the National Collection of Microorganism Cultures of "l'Institut Pasteur" (CNCM).

2. A pharmaceutical composition containing a pharmacologically efficient quantity of a Bordetella strain deficient in the production of *pertussis* toxin which, by elimination or deletion of the gene coding for the *pertussis* toxin, does not produce *pertussis* toxin, wherein said Bordetella strain expresses a hybrid protein comprising *Bordetella pertussis* filamentous hemagglutinin and a protein heterologous to said *Bordetella pertussis* filamentous hemagglutinin;

wherein said deficient Bordetella strain induces a higher production of antibodies against said filamentous hemagglutinin than the wild-type parent *Bordetella pertussis* strain; and wherein said deficient Bordetella strain colonizes lungs of an animal to which said pharmaceutical composition is administered.

3. The pharmaceutical composition according to claim 2, wherein the heterologous protein comprises at least one epitope of a protein expressed upon infections of the upper or lower respiratory tract caused by a pathogen.

4. The pharmaceutical composition according to claim 2, wherein the heterologous protein comprises at least one epitope of a protein expressed by a pathogen upon a mucosal infection.

5. The pharmaceutical composition according to claim 2, wherein the heterologous protein comprises at least one epitope of a protein expressed by a pathogen upon a systemic infection.

6. The pharmaceutical composition according to claim 2, wherein said hybrid protein comprises said *Bordetella pertussis* filamentous hemagglutinin and *Schistosoma mansoni* glutathione-S-transferase.

7. The pharmaceutical composition according to claim 2, wherein the strain belongs to *Bordetella pertussis.*

8. The pharmaceutical composition comprising a pharmacologically efficient quantity of *Bordetella pertussis* strain BPNX deposited under accession number I-1770 on Oct. 8, 1996, in the National Collection of Microorganism Cultures of "l'Institut Pasteur" (CNCM).

* * * * *

UNITED STATES PATENT AND TRADEMARK OFFICE
CERTIFICATE OF CORRECTION

PATENT NO.    : 6,660,261 B1
DATED         : December 9, 2003
INVENTOR(S)   : Natalie Mielcarek et al.

It is certified that error appears in the above-identified patent and that said Letters Patent is hereby corrected as shown below:

<u>Title page,</u>
Item [57], ABSTRACT,
Line 1, "The invention concerns a Bordetella" should read
-- The invention concerns a *Boretella*"--.
Line 3, "hemagglutin" should read -- hemagglutinin --.
Line 7, "as vaccine" should read -- as a vaccine --.

Signed and Sealed this

Third Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,660,261 B1
DATED : December 9, 2003
INVENTOR(S) : Natalie Mielcarek et al.

It is certified that error appears in the above-identified patent and that said Letters Patent is hereby corrected as shown below:

Title page,
Item [73], Assignee, please add a second assignee -- Institut National de la Sante et de la Recherche Medicale (INSERM), Paris, Cedex 13, France --.

Signed and Sealed this

Third Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,660,261 B1
DATED : December 9, 2003
INVENTOR(S) : Natalie Mielcarek et al.

It is certified that error appears in the above-identified patent and that said Letters Patent is hereby corrected as shown below:

<u>Title page,</u>
Item [57], ABSTRACT,
Line 1, "The invention concerns a *Boretella*" should read -- The invention concerns a *Bordetella* --.

Signed and Sealed this

Third Day of May, 2005

JON W. DUDAS
*Director of the United States Patent and Trademark Office*